(12) United States Patent
Thomson et al.

(10) Patent No.: US 7,433,036 B2
(45) Date of Patent: Oct. 7, 2008

(54) SPECTROMETER APPARATUS

(75) Inventors: Grant Thomson, Tarland (GB);
Graham Poulter, Orpington (GB)

(73) Assignee: Smiths Group PLC, London (GB)

( * ) Notice: Subject to any disclaimer, the term of this patent is extended or adjusted under 35 U.S.C. 154(b) by 127 days.

(21) Appl. No.: 10/595,141

(22) PCT Filed: Aug. 23, 2004

(86) PCT No.: PCT/GB2004/003607

§ 371 (c)(1),
(2), (4) Date: Mar. 3, 2006

(87) PCT Pub. No.: WO2005/024401

PCT Pub. Date: Mar. 17, 2005

(65) Prior Publication Data

US 2006/0261274 A1     Nov. 23, 2006

(30) Foreign Application Priority Data

Sep. 6, 2003   (GB) ................................. 0320925.1

(51) Int. Cl.
*G01J 3/28*     (2006.01)

(52) U.S. Cl. ....................................... 356/326; 356/445
(58) Field of Classification Search ................. 356/300, 356/326, 445
See application file for complete search history.

(56) References Cited

U.S. PATENT DOCUMENTS 5,416,573 A      5/1995   Sartor, Jr.
2002/0126290 A1*  9/2002   Naya .......................... 356/445

FOREIGN PATENT DOCUMENTS

WO     WO 02/073171 A1     9/2002

* cited by examiner

*Primary Examiner*—Gregory J Toatley, Jr.
*Assistant Examiner*—Abdullahi Nur
(74) *Attorney, Agent, or Firm*—Foley & Lardner LLP

(57) ABSTRACT

An imaging infrared spectrometer system includes an ATR unit (10) having a sample window (12) above an optical system (19) that directs radiation through the window onto the sample and directs radiation from the sample via corrective optics (40) to an imaging detector (4). The corrective optics is in the form of a wedge-shape prism (40) with a reflective surface (28) and is located near a focus of the optical system (19). The wedge prism (40) is effective to correct the focal plane orientation and anamorphic magnification at the sample.

8 Claims, 2 Drawing Sheets

SPECTROMETER APPARATUS

This invention relates to spectrometer apparatus of the kind including a radiation transparent window for supporting a sample on a surface and an optical system for directing radiation onto the sample through the window at an angle to the normal to the window surface and for receiving radiation reflected from the sample through the window.

Spectrometers, in particular, infrared spectrometers, are used extensively to analyse a wide variety of substances. Where the substance is highly absorbing, an ATR (attenuated total reflectance) unit may be used, such as the Golden Gate ATR sold by Specac Limited of Orpington, Kent, England (Golden Gate is a Registered Trade Mark of Specac Limited). This ATR unit has a diamond prism window on which the sample is placed. An arm extends over the window and carries a screw-mounted anvil, which applies a high compressive force to the sample to force it into close contact with the upper surface of the window. An optical system below the window directs a small spot of infrared radiation onto the window at an angle of about 45°. Infrared radiation is reflected at the interface between the window surface and the sample and is absorbed within a short penetration depth in the sample. Radiation reflected from the sample is collected and passed to the spectrometer detector for analysis.

Whilst such ATR units can function satisfactorily for the measurement of a single spatial point, it is desirable to increase resolution and signal-to-noise ratio.

It is an object of the present invention to provide alternative spectrometer apparatus.

According to one aspect of the present invention there is provided spectrometer apparatus of the above-specified kind, characterised in that the apparatus includes a corrective optics device arranged to increase the accuracy of imaging of the surface of the sample.

The corrective optics device preferably includes a wedge-shape prism. The corrective optics device is preferably located adjacent a focus of the optical system and is preferably located to receive radiation from the sample. The corrective optics device is preferably located adjacent a reflector and may include a reflecting surface formed on a face of the device. The apparatus may include an imaging detector arranged to receive radiation from the optical system. The apparatus may include an arm for applying pressure to urge the sample into close contact with the window surface.

According to a second aspect of the present invention there is provided a spectrometer system including a source of infra-red radiation, an analyser, an imaging detector and an ATR unit including a radiation transparent window for supporting a sample on a surface, an optical system for directing radiation onto the sample through the window at an angle to the normal to the window surface and for receiving radiation reflected from the sample through the window, characterised in that the apparatus includes a corrective wedge-shape prism located in the path of radiation to correct focal plane orientation such that it lies closer to the surface of the window.

According to a third aspect of the present invention there is provided a spectrometer system including a source of infrared radiation, an analyser, an imaging detector and an ATR unit including a radiation transparent window for supporting a sample on a surface, an optical system for directing radiation onto the sample through the window at an angle to the normal to the window surface and for receiving radiation reflected from the sample through the window, characterised in that the apparatus includes a corrective wedge-shape prism located in the path of radiation to correct anamorphic magnification at the surface of the window.

Spectrometer apparatus in the form of an ATR unit for a spectrometer system will now be described, by way of example, with reference to the accompanying drawings, in which.

The ATR unit 1 forms a part of a spectrometer system including an infrared source 2, an analyser 3 and a detector 4. The detector 4 is preferably an imaging detector such as a scanned focal plane array, such as a 64×64 pixel Javelin detector made by Raytheon of Santa Barbara, USA, each pixel measuring 60×60 μm. This detector 4 enables an image to be produced across the area of the sample being tested.

Figure 3A:
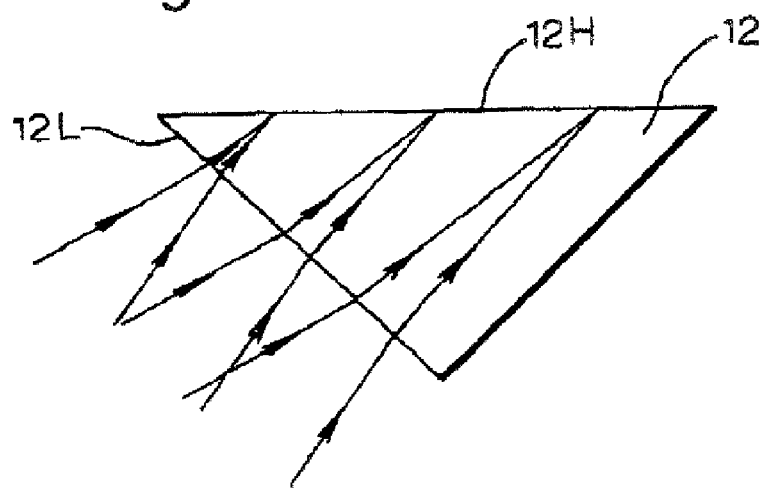
FIG. 3A is a side elevation view of the ATR sample window showing ray paths produced using the corrective optics.

The unit 1 has a housing 10 of substantially square section with an upper plate 11 supporting a small central sample window 12 (FIG. 3A) in the form of a right angle diamond prism, which is mechanically robust and infrared transparent. The prism 12 has its hypotenuse face 12H uppermost, this being the face on which the sample is placed. A clamping arm 13 is pivoted at its left-hand end 14 and has a lock 15 at its right hand end by which it can be secured with the upper plate 11. The arm 13 extends across the window 12 and has a screw-threaded rod 16 projecting down midway along its length, with a tapered anvil 17 at its lower end and a knurled knob 18 at its upper end above the arm. Once the arm 13 is locked in position, the knob 18 can be twisted to lower or raise the anvil 17.

The optical system 19 of the unit is contained within the housing 10 beneath the upper plate 11. On the left-hand wall 20 of the housing there is an entrance window 21 aligned with the source 2. The entrance window 21 is aligned along a horizontal axis with a plane mirror 22 mounted centrally of the unit and inclined at about 15° to the vertical such that radiation falling on the mirror from the window is reflected upwardly at an angle of about 30° to the horizontal and towards the left. A second plane mirror 23 is mounted on the left-hand wall 20 and is angled upwardly such that radiation incident on it is reflected upwardly towards the right at an angle of about 45° to the horizontal. An imaging lens assembly 24 is positioned adjacent the mirror 23, between the mirror and the sample window 12. The positioning and power of the imaging lens assembly 24 is such that an image of the infra-red source 2 is focused through a side face 12L of the window prism 12 onto the upper, hypotenuse surface 12H. A second, collecting lens assembly 25 is positioned below and to the right of the sample window 12 and is oriented at right angles to the imaging lens assembly 24 in line with the beam of radiation reflected from the sample on the window. A third plane mirror 26, mounted on the right-hand wall 27 of the housing 10, is angled so that the beam of radiation incident on it is reflected downwardly to the left at an angle of about 30° to the horizontal. A fourth plane reflector 28 is mounted adjacent the first mirror 22 and is inclined so that the beam of radiation incident on it is reflected to the right along a horizontal axis to an exit window 29 in the right-hand wall 27 of the housing 10. Radiation emerging from the exit window 29 is incident on the detector 4.

It will be appreciated that the transparent elements 21, 24, 25 and 29 of the optical system 19 are made of materials transparent to infrared radiation, such as ZnSe. The lens assemblies 24 and 25 are preferably multi-element in order to achieve sharp imaging across the sample area. In alternative systems it might be possible to use focusing mirrors instead of lenses.

Figure 1:
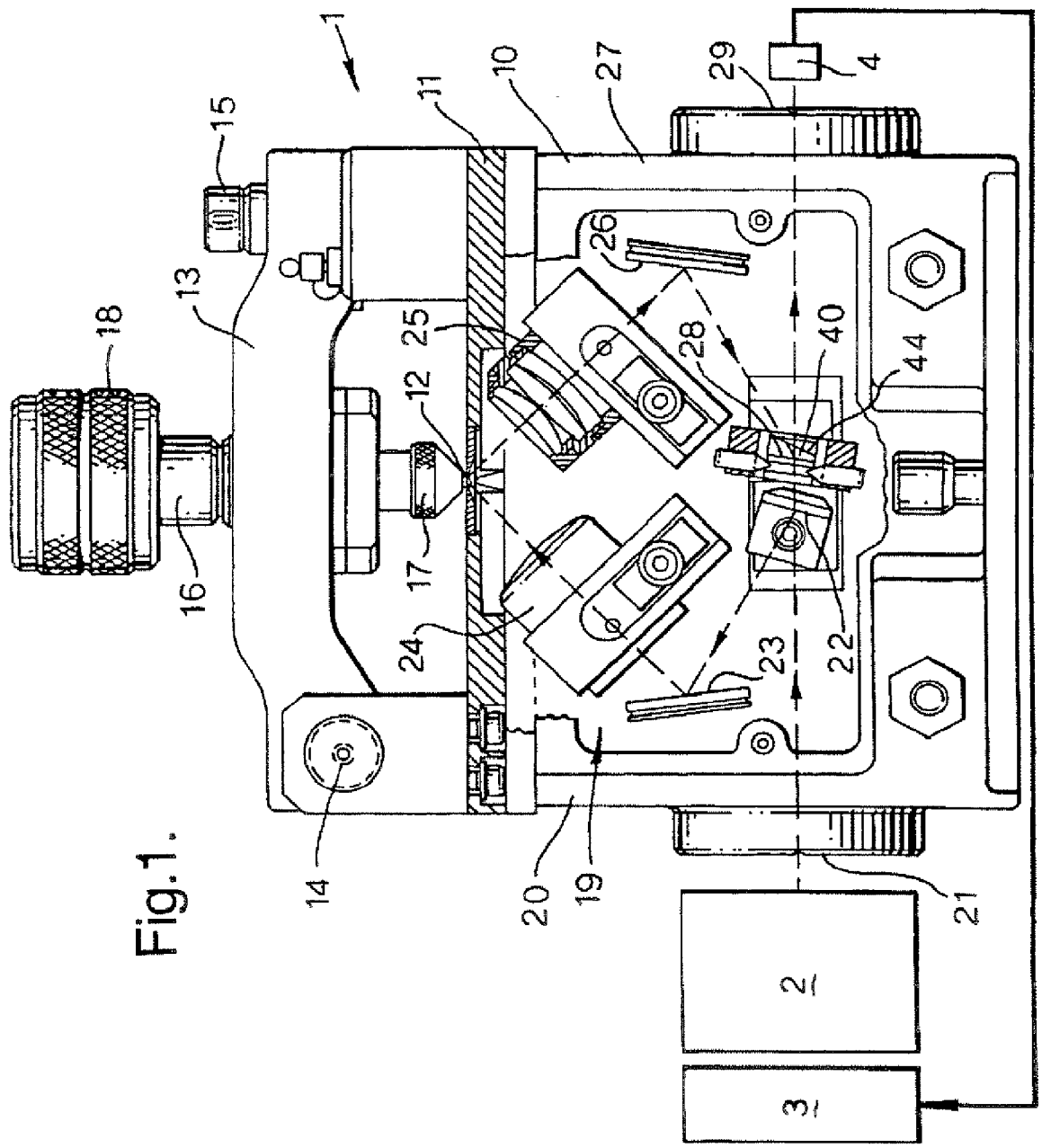
FIG. 1 is a partly sectional side elevation view of the apparatus.
Figure 2:
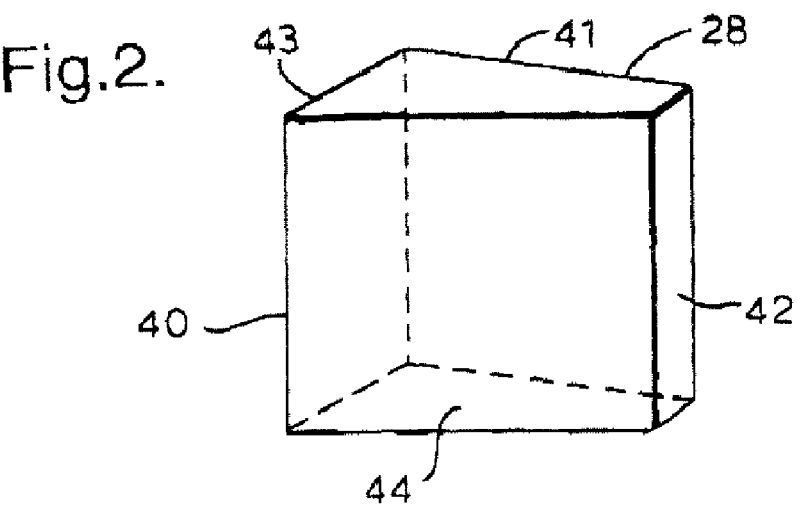
FIG. 2 is a perspective view of the wedge-shape prism corrective optics element.
Figure 3B:
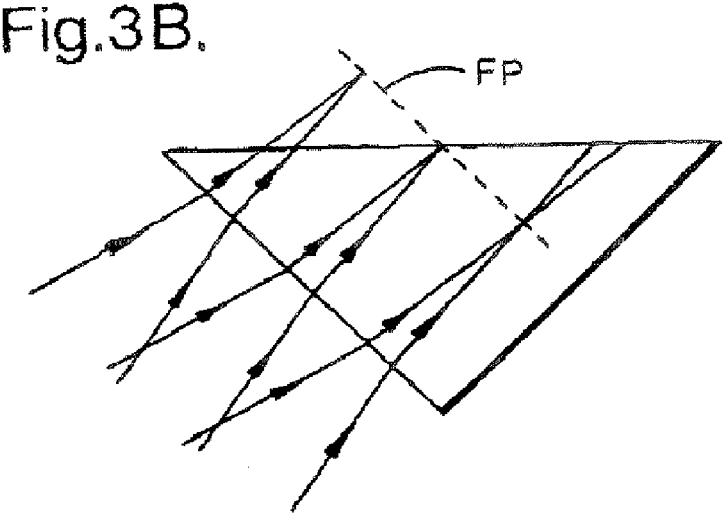
FIG. 3B is a side elevation view of the ATR sample window showing typical ray paths that would be produced in the absence of the corrective optics.

As so far described, the optical system 19 is substantially conventional. With such an arrangement, the focal plane would typically not be coplanar with the sample face 12H but could be inclined relative to it as shown by the broken line FP in FIG. 3B. The system, however, includes corrective optics provided a wedge-shape prism 40 of ZnSe or other infrared-transparent material located in the path of rays reflected from the sample. As shown most clearly in FIG. 2, the prism 40 has a rear face 41 substantially square in shape and two edge faces 42 and 43 projecting from the rear face at substantially right angles. One edge face 42 is narrower than the other 43 so that the front face 44 of the prism 40 is inclined relative to the rear face an angle of about 15°. The prism 40 is formed as a single unit with the reflector 28, which is provided by a reflecting surface on the rear face 41 of the prism. The prism 40 is oriented with its edges 42 and 43 extending parallel to the z axis, that is, normal to the plane of the paper, with the two larger, angled faces 41 and 44 extending generally transversely of the ray path between the mirror 26 and the exit window 29. The narrower edge 42 is located lower than the wider edge 43 so that the front face 44 presents a greater angle of incidence to the incident ray from the mirror 26 than does the rear face 41. The wedge prism 40 is tilted so that the ray incident on it makes an angle of about 24° to the normal to the front face 44. It can be seen that the light is refracted by the front face 44 of the wedge 40, transmitted through to the rear surface 41, reflected from the mirror coating 28 and refracted out of the front surface again.

Without the wedge prism 40, the sample surface would not be formed correctly over its whole area and would suffer anamorphic distortion. For example, a circular sample would appear to be elliptical. This may not be important where the apparatus is used only to make macroscopic measurements of the sample but they become particularly important where the sample is imaged and spectrometric analysis is made at different points across the image, as is now possible using elemental area array detectors.

The wedge prism 40 provides relatively simple corrective optics that can be incorporated into the existing system with minimal losses. The wedge prism 40 can correct the focal plane orientation so that it is co-planar with the sampling face 12H of the diamond window 12 and thereby correct the anamorphic magnification of the conventional system. By appropriately selecting the angle of the wedge 40 and its tilt it is possible to achieve an optimum correction of both focal plane tilt and anamorphic magnification. The wedge prism 40 can also help correct for chromatic aberration for the infrared radiation wavelengths typically used across the entire face of the sampling window. The wedge prism 40 also enables a minimisation of the resolvable area when using elemental area, array detectors and can increase the signal-to-noise ratio.

The best location for the corrective wedge prism is near a focus of the optical system, which, in the particular system described, is near the lower, exit reflector 28. In a different system, the corrective optics may need to be positioned differently according to the locations of the foci. It is not essential for the corrective optics to be reflective, as described above, instead an entirely transmissive element could be used. In some applications it may be preferred to use more than one corrective optics element. It might be possible to position the corrective optics in the path of radiation supplied to the sample instead of to receive radiation from the sample.

The invention claimed is:

1. A spectrometer apparatus comprising:
   (a) a radiation transparent window for supporting a sample on a surface;
   (b) an optical system for directing radiation onto the sample through the window at an angle to the normal to the window surface and for receiving radiation reflected from the sample through the window; and
   (c) a corrective optics device comprising (i) a wedge-shape prism and (ii) a focusing device intermediate the sample supporting surface and the prism such that the prism is adjacent a focus of the optical system and arranged to increase the accuracy of imaging of the surface of the sample.

2. The spectrometer apparatus according to claim 1, wherein the prism is located to receive radiation from the sample.

3. The spectrometer apparatus according to claim 1, wherein the prism is located adjacent to a reflector.

4. The spectrometer apparatus according to claim 3, wherein the prism has a reflecting surface formed on a face of the device.

5. The spectrometer apparatus according to claim 1, further comprising an imaging detector arranged to receive radiation from the optical system.

6. The spectrometer apparatus according to claim 1, further comprising an arm for applying pressure to the sample to urge the sample into close contact with the window surface.

7. An spectrometer system comprising:
   (a) a source of infrared radiation;
   (b) an analyser;
   (c) an imaging detector; and
   (d) an attenuated total reflectance (ATR) unit comprising (i) a radiation transparent window for supporting a sample on a surface and (ii) an optical system for directing radiation onto the sample through the window at an angle to the normal to the window surface and for receiving radiation reflected from the sample through the window,
   wherein the apparatus includes a corrective wedge-shape prism and an imaging lens located between the prism and the window, and
   wherein the prism is located in the path of radiation to correct focal plane orientation such that it lies closer to the surface of the window.

8. An spectrometer system comprising:
   (a) a source of infrared radiation;
   (b) an analyser,
   (c) an imaging detector and
   (d) an attenuated total reflectance (ATR) unit comprising (i) a radiation transparent window for supporting a sample on a surface and (ii) an optical system for directing radiation onto the sample through the window at an angle to the normal to the window surface and for receiving radiation reflected from the sample through the window,
   wherein the apparatus includes a corrective wedge-shape prism and an imaging lens located between the prism and the window, and
   wherein the prism is located in the path of radiation to correct anamorphic magnification at the surface of the window.

* * * * *